(12) United States Patent
Schlegel

(10) Patent No.: US 12,121,210 B2
(45) Date of Patent: Oct. 22, 2024

(54) VIDEO ENDOSCOPE AND ENVELOPE FOR A VIDEO ENDOSCOPE AND METHOD FOR MONITORING A STERILE BARRIER OF A VIDEO ENDOSCOPE

(71) Applicant: ALPAKA TECHNOLOGY UG (haftungsbeschränkt), Denzlingen (DE)

(72) Inventor: Marco Schlegel, Denzlingen (DE)

(73) Assignee: ALPAKA TECHNOLOGY UG (haftungsbeschränkt), Denzlingen (DE)

( * ) Notice: Subject to any disclaimer, the term of this patent is extended or adjusted under 35 U.S.C. 154(b) by 121 days.

(21) Appl. No.: 17/710,306

(22) Filed: Mar. 31, 2022

(65) Prior Publication Data
US 2022/0313066 A1 Oct. 6, 2022

(30) Foreign Application Priority Data
Mar. 31, 2021 (DE) .......................... 102021108188.2

(51) Int. Cl.
*A61B 1/00* (2006.01)
(52) U.S. Cl.
CPC ...... *A61B 1/00094* (2013.01); *A61B 1/00142* (2013.01)
(58) Field of Classification Search
CPC ............ A61B 1/00094; A61B 1/00142; A61B 1/00–32
See application file for complete search history.

(56) References Cited

U.S. PATENT DOCUMENTS 4,757,381 A * 7/1988 Cooper .............. A61B 1/00142
433/116
5,732,712 A * 3/1998 Adair ..................... A61B 90/50
128/853
(Continued)

FOREIGN PATENT DOCUMENTS

CN 211213047 U 9/2019
CN 110811777 A 2/2020
(Continued)

OTHER PUBLICATIONS

Aesculap EndoSheath by Aesculap AG—a B.Braun band of Tuttlingen, Germany, brochure 56 pages, EndoSeath described on p. 8, www.aesculap.de; 2022 https://www.google.de/url?sa=t&rct=j&q=&esrc=s&source=web&cd=&ved=2ahUKEwiG9vTR19b3AhWWhf0HHXBMA1kQFnoECAIQAQ&url=https%3A%2F%2Fwww.bbraun.de%2Fcontent%2Fdam%2Fcatalog%2Fbbraun%2FbbraunProductCatalog%2FS%.
(Continued)

*Primary Examiner* — John P Leubecker
*Assistant Examiner* — Jae Woo
(74) *Attorney, Agent, or Firm* — Nath, Goldberg & Meyer; Jerald L. Meyer; Morgan D. Rosenberg

(57) ABSTRACT

The invention relates to a video endoscope (10) with an endoscope (20) comprising endoscope optics (22) and a camera head (30) comprising camera electronics (35) and a display and control unit (36), wherein a vacuum pump (40) is arranged in the video endoscope (10) for aspiration of air from the environment of the video endoscope (10).
Further, the invention relates to an envelope (70) suitable to receive a video endoscope (10) comprising a hollow tube (71) having a distal end (71*a*) and a proximal end (71*b*), wherein the distal end (71*a*) is closed by means of an optically transparent window (72), wherein a flexible pouch (73) having an inlet opening (74) is arranged at the proximal (Continued)

Figure 1:
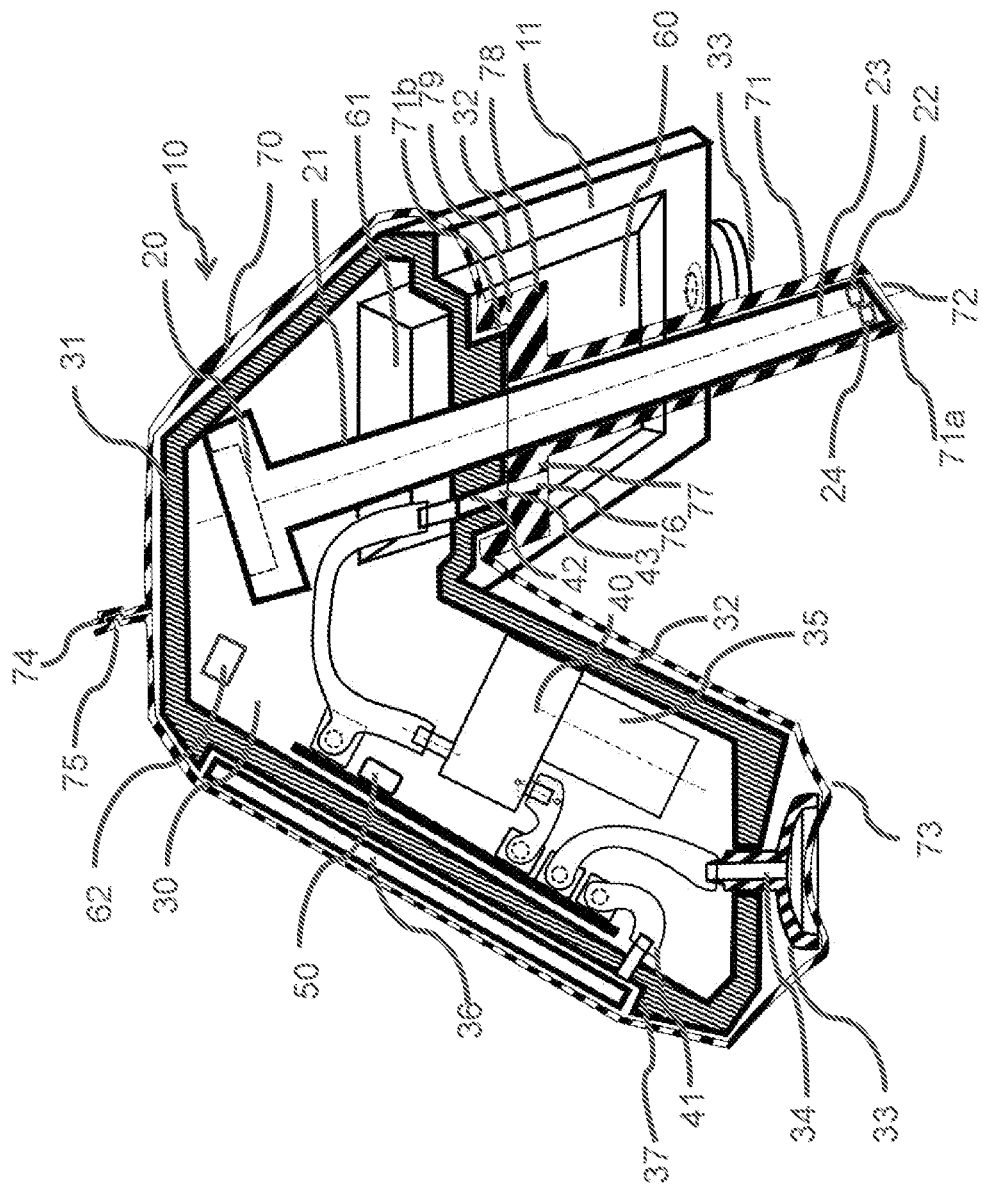

end (71b), wherein the inlet opening (74) of the pouch (73) is implemented to be closable by means of a closure (75).

21 Claims, 7 Drawing Sheets

(56) References Cited

U.S. PATENT DOCUMENTS

| | | | |
|---|---|---|---|
| 5,957,832 | A | 9/1999 | Taylor et al. |
| 6,447,444 | B1* | 9/2002 | Avni ................. A61B 1/00151 600/129 |
| 6,508,759 | B1 | 1/2003 | Taylor et al. |
| 6,845,775 | B1 | 1/2005 | Barthes |
| 8,886,331 | B2 | 11/2014 | Labadie et al. |
| 2001/0025133 | A1* | 9/2001 | Staud ................. A61B 1/0051 600/121 |
| 2003/0083548 | A1 | 5/2003 | Ouchi et al. |
| 2008/0021276 | A1* | 1/2008 | Wax ................. A61B 1/00142 600/122 |
| 2008/0132763 | A1* | 6/2008 | Isaacson ............ A61M 3/0201 600/158 |
| 2018/0271356 | A1* | 9/2018 | Antonioli .......... A61B 1/00128 |
| 2018/0271581 | A1 | 9/2018 | OuYang et al. |
| 2019/0105139 | A1* | 4/2019 | Zhou ................. A61C 17/224 |
| 2019/0193122 | A1* | 6/2019 | Liu ........................ B08B 3/02 |
| 2020/0178763 | A1* | 6/2020 | Tilson ............... A61B 1/00042 |
| 2022/0117471 | A1* | 4/2022 | Antonioli .......... A61B 1/00006 |
| 2022/0125474 | A1* | 4/2022 | Zhou ..................... A61B 17/42 |
| 2022/0409318 | A1* | 12/2022 | Perez ...................... A61B 46/17 |
| 2023/0346205 | A1* | 11/2023 | Tilson ............... A61B 1/00057 |

FOREIGN PATENT DOCUMENTS

| | | |
|---|---|---|
| CN | 110960780 A | 4/2020 |
| CN | 201250005 U | 4/2020 |
| DE | 102014111354 A1 | 2/2016 |
| EP | 2133036 B1 | 11/2011 |
| EP | 2842511 A1 | 3/2015 |
| EP | 2139377 B1 | 8/2017 |
| JP | 2015-009050 A | 1/2015 |
| JP | 2019-130005 A | 8/2019 |
| WO | 98/02107 A1 | 1/1998 |
| WO | 98/23216 A1 | 6/1998 |
| WO | 2020/148725 A1 | 7/2020 |

OTHER PUBLICATIONS

Medtronic's ENT Scopie Sheath Proves Effective for Germicidal Protedtion—Medgadget, Feb. 8, 2010; www.medgadget.com/2010/02/medtronics_ent_scope Sheath_pro.

Clearview II Flexible Endoscope Cover by Invotec International, Inc.Jacksonville, Florida, USA; https://www.invotec.net/products/endoscope_covers.html; Apr. 29, 2022.

New MEDTRONIC 226401 Slide-On Endosheath System (X) 226401 Disposables by DOTmed Apr. 29, 2022; https://de.dotmed.com/listing/disposables-general/mdtronic/226401-slide-on-endoshearth-system.

Summons to oral hearing issue May 23, 2022, in parallel German patent application No. 10 2021 108 188.2.

Office Action issued Jan. 13, 2022, in corresponding German application No. 10 2021 108 188.2.

* cited by examiner

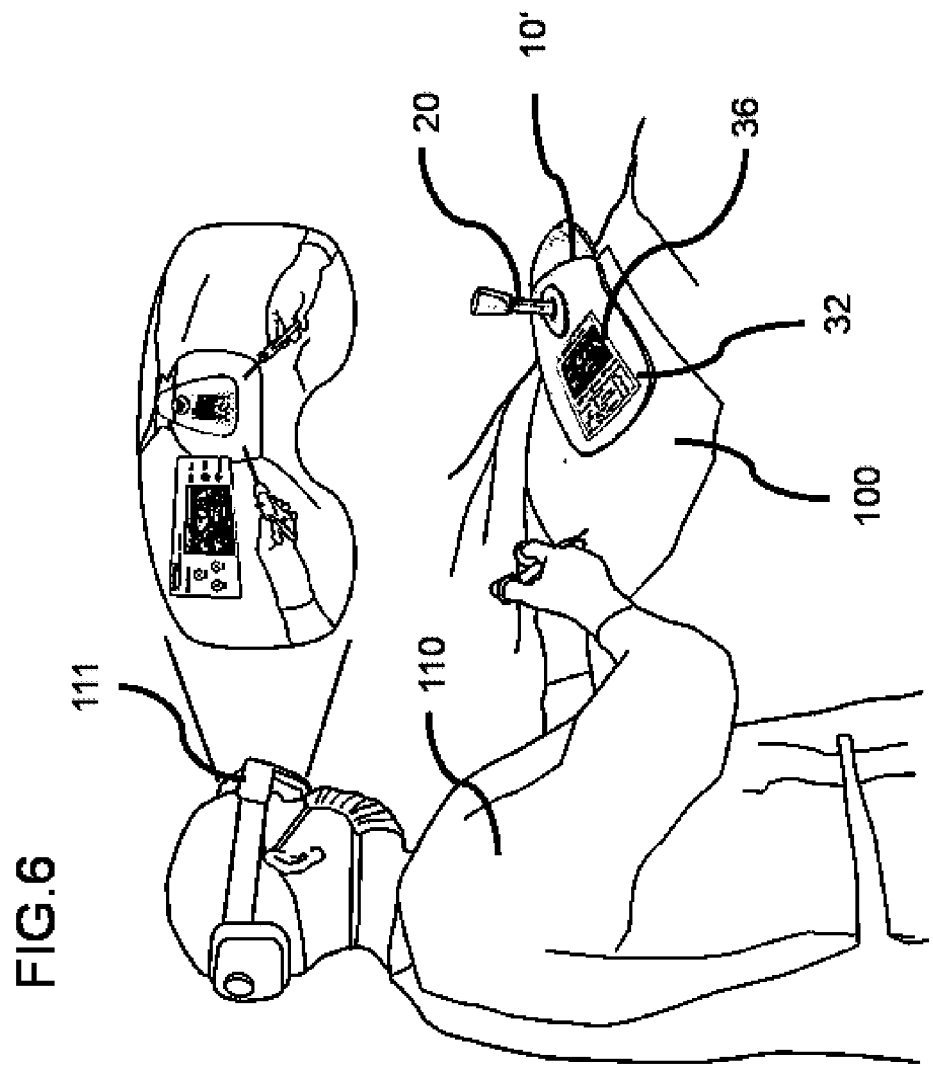

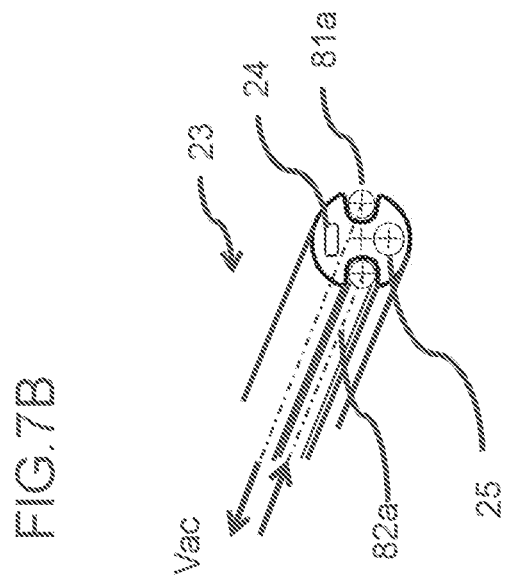
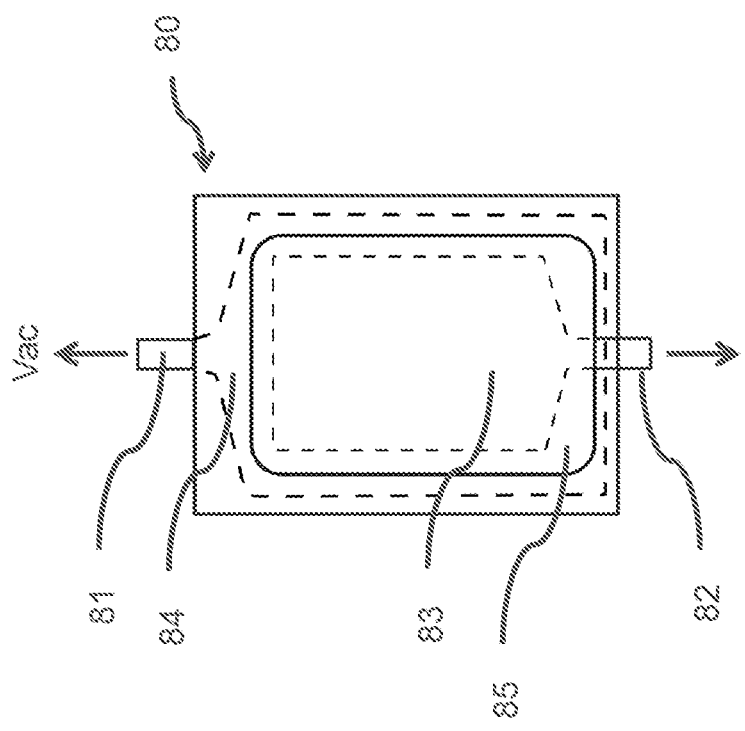
FIG.7B
FIG.7A

VIDEO ENDOSCOPE AND ENVELOPE FOR A VIDEO ENDOSCOPE AND METHOD FOR MONITORING A STERILE BARRIER OF A VIDEO ENDOSCOPE

Video endoscopes having an endoscope comprising endoscope optics and a camera head comprising camera electronics and a display and control unit are known.

The disadvantage of known systems is the complicated hygiene concept brought about by the large number of different components, which are partly autoclaved, partly chemically cleaned and partly separated from the patient by a disposable sterile cover. This results in high costs for materials and labor.

For example, disposable sterile covers for video endoscope envelopes with a hollow tube having a distal end and a proximal end are known, wherein the distal end is closed by means of an optically transparent window, wherein a flexible pouch having an inlet opening is arranged at the proximal end. The endoscope can be inserted through the inlet opening. Supply lines can be routed through the pouch, which is open towards the proximal end. The camera head is accessible through the open pouch and must be cleaned separately.

The task of the invention consists in the provision of a video endoscope which enables an improved hygiene concept.

The task is solved according to the invention by a video endoscope with the features of claim 1, by an envelope for a video endoscope with the features of claim 13, and by a method for monitoring a sterile barrier of a video endoscope.

Advantageous embodiments and further developments of the invention are given in the dependent claims.

The video endoscope according to the invention with an endoscope comprising endoscope optics and a camera head comprising camera electronics and a display and control unit is characterized in that a vacuum pump for aspiration of air from the environment of the video endoscope is arranged in the video endoscope. It is essential for the invention that the vacuum pump is integrated in the video endoscope and thus aspirate air from the environment of the video endoscope into the video endoscope. Such an arrangement makes it possible to suction an envelope, in particular if it is closed air-tight, against the surface of the video endoscope, since air can be suctioned from the environment of the video endoscope by means of the vacuum pump and thus from the intermediate space between the envelope and the video endoscope, and thus, for example, to provide a closed sterile barrier around the video endoscope, which simplifies the preparation of the video endoscope for operations. An aspirated envelope, in particular over the camera head, can have the advantage of being less obtrusive and still allowing operation of the camera head.

Preferably, the video endoscope comprises a housing in which the vacuum pump is arranged, wherein the suction opening for the vacuum pump is arranged in the wall of the housing.

In a preferred embodiment, an exhaust air opening is arranged in the wall of the housing, which has a connecting element to an exhaust valve of an envelope for the video endoscope. This provides the possibility to remove the aspirated air from the video endoscope, including from the envelope.

According to an alternative preferred embodiment, a compressed air container is provided for receiving the aspirated air. The aspirated air thus remains in the video endoscope and can be used, for example, for air cooling of heat-critical components or as an additional pneumatic energy source, in particular on both the pressure and the vacuum side of the vacuum pump.

A particularly preferred embodiment of the invention provides that the video endoscope has at least one pressure sensor, for example for determining the ambient pressure. Monitoring of the operation of the sterile barrier can be made possible by means of such a pressure sensor. Furthermore, a suction pressure can, for example, be monitored at the patients or at other pneumatic applications.

Particularly preferably, the video endoscope has a wireless power supply, which preferably comprises at least one accumulator or at least one battery. Such a design eliminates the need for a pressure-tight feed-through of the power supply through an envelope.

Advantageously, the video endoscope has a radio interface. Using such an embodiment, a pressure-tight feed-through of data transmission lines through an envelope can be dispensed with.

Preferably, the housing has at least one adjustable foot, preferably three adjustable feet, which has at least one suction cup, which is preferably connected to the vacuum pump. The housing can be securely placed on the patient by means of the adjustable feet. The suction cup or cups can ensure a secure placement. The application of vacuum pressure to the suction cup or cups by the vacuum pump can increase stability. In particular, this enables safe and reliable positioning of the housing directly on the patient without the need for another operator to hold the video endoscope and without the need for a cost-intensive support arm or robot to position the video endoscope.

According to a preferred embodiment of the invention, the display and control unit comprises a touch display. This can be operated easily and reliably even when the envelope is in place, in particular when the envelope is aspirated and can be applied to the touch display without folds.

Advantageously, the display and control unit is surrounded by a circumferential edge, wherein at least one suction opening of the vacuum pump is arranged in the circumferential edge. Such a configuration can favor the fold-free application of the envelope to the display and control unit, especially if this is implemented as a touch display. Since the display and control unit is advantageously arranged directly at the site of the operation, as the camera head can be placed directly on the patient, this can also lead to improved eye-hand coordination when the live image of the video endoscope is displayed directly on the display element.

Advantageously, a vacuum bag which is connectable to the vacuum pump is provided and in which vacuum bag a flushing fluid bag is arranged. This makes it possible to use the vacuum pump to control other functions, such as a flushing or cleaning operation.

Preferably, the endoscope is detachably connected to the camera head and can be locked in place by the vacuum pump. Such a design allows easy exchange of the optics for different application purposes. A locking in place by means of negative pressure can provide a reliable fixation.

The envelope according to the invention, suitable to receive a video endoscope comprising a hollow tube having a distal end and a proximal end, wherein the distal end is closed by means of an optically transparent window, wherein a flexible pouch having an inlet opening is arranged at the proximal end, is characterized in that the envelope comprises an exhaust valve. Such an exhaust valve enables air to be discharged from the interior of the envelope.

According to a preferred embodiment of the invention, the exhaust valve has a connecting element to an exhaust air opening of a vacuum pump of a video endoscope arrangeable in the envelope. This allows the air to be led out of the interior of the envelope by means of a vacuum pump arranged inside the video endoscope.

Preferably, the exhaust valve is implemented as a one-way check valve to prevent air from flowing back through the exhaust valve into the interior of the envelope.

Preferably, the inlet opening of the bag is implemented to be closable by means of a closure. The closable inlet opening enables the complete enclosure of the video endoscope by the envelope and the application of a negative pressure for aspiration of the envelope to the surface of the video endoscope, in particular on all surfaces, especially preferably on the operating elements.

According to a preferred embodiment of the invention, the hollow tube has a circumferential collar at its proximal end in which the exhaust valve is arranged. Such a configuration allows a sturdy arrangement of the exhaust valve.

Advantageously, the hollow tube is made of metal or a similarly sturdy material that is resistant to tension and pressure. This enables high stability of the envelope.

Preferably, the pouch is made of a transparent plastics material. This allows a flexible attachment to different shapes of the housing of the video endoscope, in particular the camera head, and there, especially, to the display and control element.

Suction can be improved if a channel is preferably arranged in the hollow tube running between the distal end and the proximal end.

According to the invention, a video endoscope according to the invention comprises an envelope according to the invention.

Particularly preferably, the hollow tube of the envelope is detachably fixable to the video endoscope, in particular to the housing, especially preferably to the camera head, preferably by means of a mechanical quick-release fastener, especially preferably a bayonet lock. In this way, a reliable arrangement can be achieved and, in particular, it can be avoided that the envelope is undesirably shifted against the video endoscope during an operation.

According to a particularly advantageous embodiment of the invention, an exhaust air opening is arranged in the wall of the housing of the video endoscope, which comprises a connecting element to an exhaust valve of the envelope for the video endoscope, and an exhaust valve is arranged in the envelope for the video endoscope, which comprises a connecting element to the exhaust air opening of the housing of the video endoscope, wherein upon fixation of the hollow tube to the video endoscope, the connecting element of the exhaust air opening and the connecting element of the exhaust valve are coupled. The handling of the video endoscope can be simplified by such an arrangement, in particular during the preparation of the operation.

The method according to the invention for monitoring the sterile barrier in a video endoscope with an envelope according to the invention comprises the following steps:
  Insertion of the video endoscope into the envelope,
  Creation of a vacuum in the envelope,
  Detection of the pressure in the envelope and comparing the pressure with a predetermined threshold value, and
  Issuance of an alarm signal when the prevailing pressure exceeds the threshold value.

Such a method provides a simple means of monitoring whether the sterile barrier is intact during surgery and can contribute to patient safety.

Preferably, the envelope is closed after insertion of the video endoscope into the envelope.

According to an advantageous further development, the video endoscope is positioned on a patient. This enables easier handling.

Particularly preferably, the video endoscope has a housing with at least one adjustable foot, preferably three adjustable feet, which adjustable foot has at least one suction cup, which is suctioned onto the patient in a further step. In this way, a particularly safe positioning of the video endoscope can be achieved.

Preferably, an alarm signal is issued when the suction cup is released from the patient. An operator can thereby receive an indication of a repositioning of the video endoscope.

Figure 4:
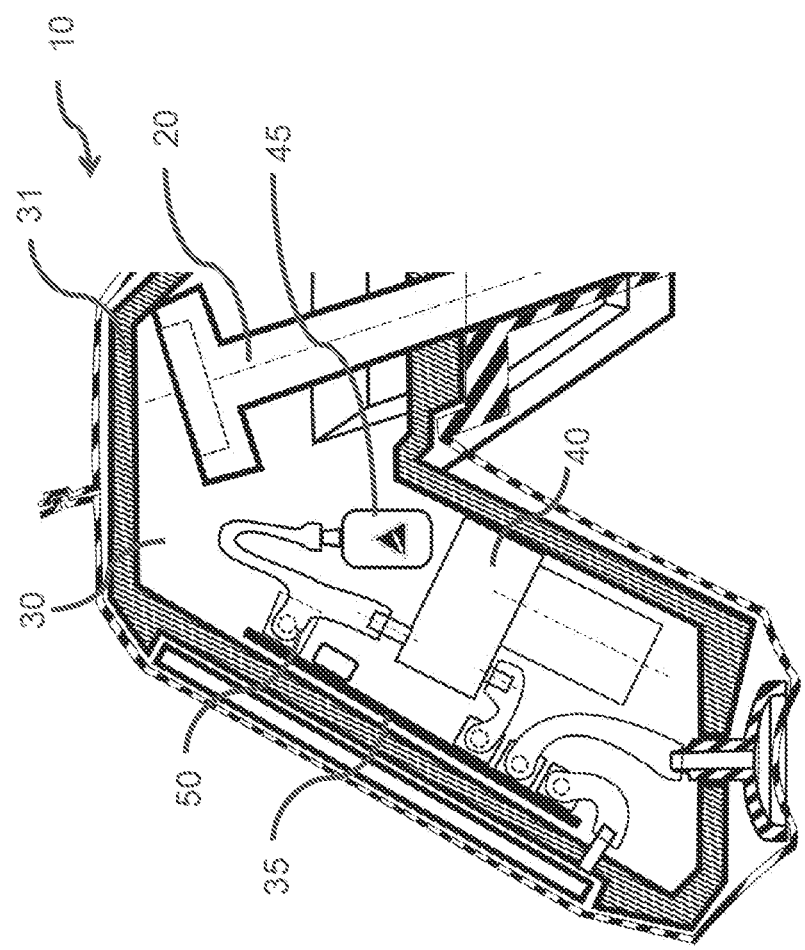
Figure 5:
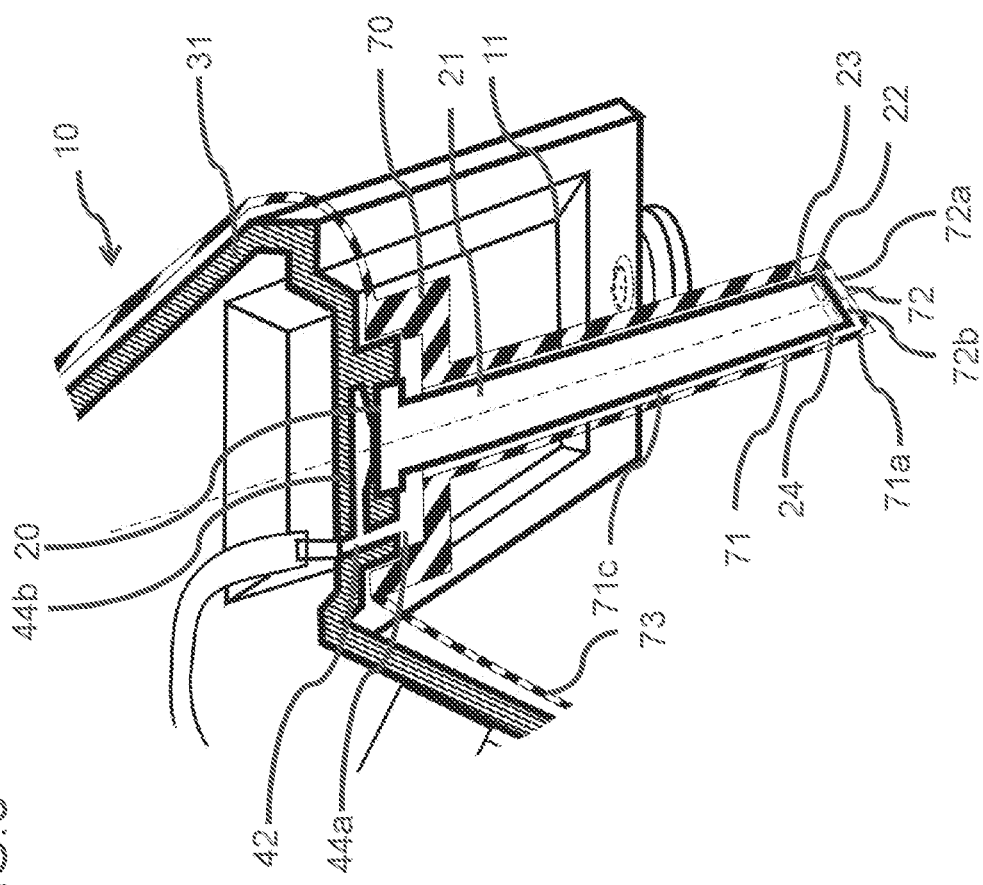

An embodiment example of the invention is explained in detail with reference to the following figures. Wherein, FIG. 1 shows a cross-section through a first embodiment example of a video endoscope according to the invention with an envelope according to the invention, FIG. 2 shows a perspective view of the video endoscope according to FIG. 1, FIG. 3 shows a sectional enlargement of the video endoscope according to FIG. 2, FIG. 4 shows a cross-section through a second embodiment of a video endoscope according to the invention with an envelope according to the invention, and FIG. 5 shows a cross-section through a third embodiment of a video endoscope according to the invention with an envelope according to the invention, FIG. 6 shows a perspective view of a fourth embodiment of a video endoscope according to the invention in an application, FIG. 7a shows a schematic representation of a flushing device for a video endoscope according to any one of FIGS. 1 to 6, and FIG. 7b shows a schematic representation of a distal end of the shaft of the endoscope of a video endoscope according to any one of FIGS. 1 to 6.

Figure 2:
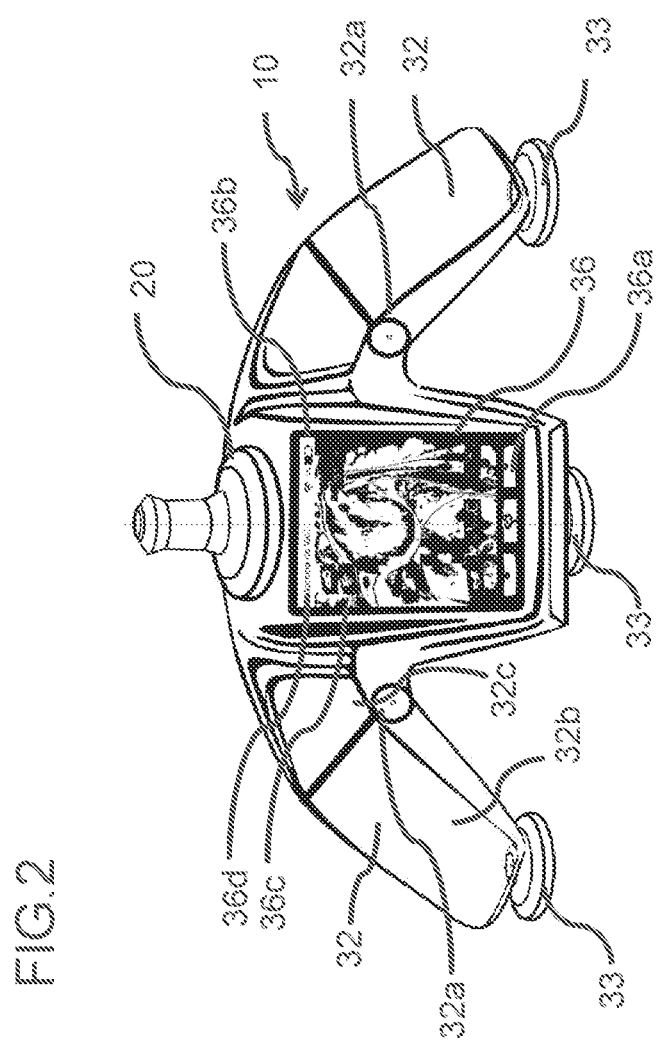
Figure 3:
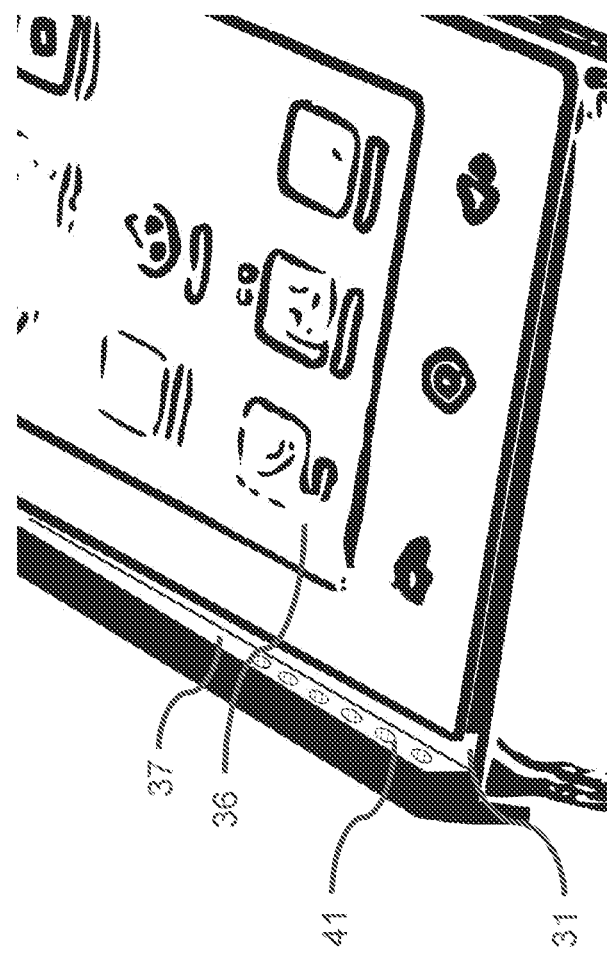

FIG. 1 shows a cross-section through a first embodiment example of a video endoscope 10 according to the invention with an envelope 70 according to the invention, wherein FIG. 2 and FIG. 3 show views of the video endoscope 10.

The video endoscope 10 has an endoscope 20 and a camera head 30. The endoscope 20 comprises endoscope optics 22, which are, in particular, arranged in a shaft 23. The camera head 30 comprises at least camera electronics 35 and a display and control unit 36. Furthermore, an endoscope light source 24 can be arranged in the shaft 23.

The endoscope 20 and the camera head 30 may be arranged in a housing 11 of the video endoscope 10. Alternatively, the endoscope 20 and the camera head 30 may be detachably connected to each other, wherein the endoscope 20 is arranged in a housing 21 and the camera head 30 is arranged in a housing 31. In this case, the housing 11 of the video endoscope 10 includes the housing 21 of the endoscope 20 and the housing 31 of the camera head 30.

The detachable connection can be made, for example, by means of negative pressure generated in particular by means of the vacuum pump 40, as shown in the embodiment example of FIG. 5. For this purpose, a further suction opening 41 can be arranged in the housing 31, by means of which a vacuum can be generated in an intermediate space 44b between the housing 21 of the endoscope 20 and the housing 31 of the camera head 30.

In the video endoscope 10, in particular in the housing 11, for example, in the housing 31 of the camera head 30, a vacuum pump 40 is arranged for aspiration of the air from the environment of the video endoscope 10. A suction opening 41 for the vacuum pump 40 may be arranged in the wall of the housing 11, for example, in the wall of the housing 31 of the camera head 30. If the video endoscope 10 is surrounded by an envelope 70 described in more detail below, the vacuum pump 40 can be used to draw air from the intermediate space between the video endoscope 10 and the envelope 70 and to draw the envelope 70 against the surface of the video endoscope 10.

The aspirated air can be suctioned out of the housing 11 and out of the envelope 70 by the vacuum pump 40. For this purpose, the exhaust air opening 42 arranged in the wall of the housing 11 or alternatively housing 31 may comprise a connecting element 43 to an exhaust valve 76 of the envelope 70 for the video endoscope 10.

Alternatively, as shown in FIG. 4, in a second embodiment example of the video endoscope 10, a compressed air container 45 may be provided for receiving the aspirated air in the housing 11, in particular in the housing 31.

The video endoscope 10 may comprise a pressure sensor 50 for determining the ambient pressure. This pressure sensor is arranged, for example, in the housing 11, in particular in the housing 31 of the camera head 30, in such a way that it can determine the pressure at the outer surface of the housing 11 or alternatively housing 31, in particular when the envelope 70 is in place in the intermediate region between the video endoscope 10 and the envelope 70. The video endoscope 10 may comprise further pressure sensors which are not shown, for example, in the exhaust air opening, so that by measuring the pressures or detecting differential pressures, warning or control signals may be generated and issued.

The video endoscope 10 may comprise a wireless power supply 60, which preferably comprises an accumulator 61 or a battery. The accumulator 61 is advantageously implemented to be rechargeable on a charging station, for example when the video endoscope 10 is not in use.

Furthermore, the video endoscope 10 may comprise a radio interface 62, by means of which, for example, the images detected by the endoscope 20 can be transmitted to a screen in the operating room.

The housing 11, in the present embodiment example, the housing 31, may comprise at least one adjustable foot 32, in the embodiment example, three adjustable feet 32. Each of the adjustable feet 32 may comprise at least one suction cup 33. The suction cups 33 may comprise a suction opening 34 through which air can be aspirated by means of the vacuum pump 40. The envelope 70 is thereby suctioned into the suction cups 33, which can improve the contact of the suction cups with the body of the patient. One or more of the adjustable feet 32 may comprise two sub-segments 32b, 32c, which are connected to each other by means of an articulation 32a, preferably a swivel articulation, in order to be able to optimally apply the housing 11 to the patient. In particular, this can be done directly, so that neither an additional operator nor a support arm or robot is required for this (see also FIG. 6).

The display and control unit 36, which is arranged in particular on the outside of the housing 11, here the housing 31, can comprise a touch display 36. The display and control unit 36 can be used to switch the endoscope 20 on and off, to start and stop image acquisition by means of the endoscope 20, or to control data transmission from the video endoscope 10 to a screen or processing unit in the operating room. The display and control unit 36 can also be used, for example, to switch the vacuum pump 40 on and off via a command button 36a. The touch display 36 may also comprise display elements 36b that provide information about, for example, the state of charge of the accumulator 61 or the quality of the radio signal. There may, in particular, be a display element 36c that indicates the pressure in the intermediate space between the video endoscope 10 and the envelope 70. There may, alternatively or additionally, be a display element 36d to provide a warning signal if the pressure in the intermediate space between the video endoscope 10 and the envelope 70 rises beyond a predetermined threshold, thereby warning that the envelope 70 is not air-tight and that the sterile barrier intended to be created by the envelope 70 may not be dependable. Other pressure indicators and/or warning indicators may furthermore be provided, for example, indicating the pressure exerted on one or preferably all of the suction cups 33 or indicating evaluations made based thereon.

The display and control unit 36, in particular the touch display, may be surrounded by a circumferential edge 37. This edge 37 can, for example, be formed by a circumferential projection. Alternatively, this edge 37 can also be part of a recess arranged in the housing 11. This allows for a surface of the housing 11 that is as uniform as possible, without steps. The suction opening 41 or one of several suction openings 41 may be arranged in the circumferential edge 37 or in the bottom area below the recess, which may improve suction of the envelope 70 to the display and control unit 36 without folds.

The envelope 70 according to the invention comprises a hollow tube 71 having a distal end 71a and a proximal end 71b, the distal end 71a being closed by means of an optically transparent window 72. The hollow tube 71 may, for example, be made of metal or a similarly sturdy material that is resistant to tension and pressure. The window 72 is preferably made of glass or a transparent plastics material. If a vacuum is generated within the envelope 70, the window 72 is preferably suctioned flat against the distal end of the shaft 23. FIG. 5 shows an alternative configuration in which a spacer 72a can be arranged between the window 72 and the distal end of the shaft 23, for example, by thickening the window 72, in particular in the area in front of the endoscope optics 22, which spacer 72a also causes a free space 72b in front of the distal end of the shaft 23 even when the envelope 70 is suctioned onto the shaft 23, which can result in isolation of the vacuum, for example, in particular of the endoscope light source 24, which can be arranged next to the endoscope optics 22.

Generally, the vacuum can be created by aspiration of air through the annular gap between the inside of the hollow tube 71 and the outside of the shaft 23. The suction can be improved if a channel 71c is arranged, for this purpose, in the hollow tube 71 running between the distal end 71a and the proximal end 71b. A channel (not shown) may also additionally or alternatively, be arranged in the shaft 23 between the distal end of the shaft 23 and the proximal end of the shaft 23, through which air can be suctioned from the distal to the proximal end of the shaft 23.

A flexible pouch 73 is arranged at the proximal end 71b of the hollow tube 71, which can be made, for example, of a transparent plastics material, in particular a plastic film. The pouch 73 encloses the hollow tube 71 in such a way that the interior of the pouch 73 is in communication with the interior of the hollow tube 71. The connection between the pouch 73 and the hollow tube 71 is, in particular, implemented to be airtight. The pouch 73 has an inlet opening 74 which is implemented to be closable, in particular in an airtight manner, by means of a closure 75. The closure 75 can, for example, be implemented as a zip-lock closure.

The envelope 70 has an exhaust valve 76, which can be implemented, in particular, as a one-way check valve. The hollow tube 71 may comprise a circumferential collar 78 at its proximal end 71b, in which the exhaust valve 76 may be arranged.

The exhaust valve 76 may comprise a connecting element 77 to the exhaust air opening 42 of the vacuum pump 40 of the video endoscope 10 that can be arranged in the envelope 70.

The envelope 70 may be used in the following manner: the video endoscope 10 can be inserted into the envelope 70 through the inlet opening 74, in particular, in such a way that the endoscope 20 comes to rest in the hollow tube 71 and the camera head 30 is arranged in the pouch 73. A fixation of the hollow tube 71 to the housing 11 of the video endoscope 10, in particular, the housing 31 of the camera head 30 of the video endoscope 10, may occur by means of a mechanical quick-release fastener such as a bayonet lock 79, which lock may be arranged, for example, between the collar 78 of the hollow tube 71 and the housing 11, in particular the housing 31. Alternatively, a fixation of the hollow tube 71 to the housing 11 of the video endoscope 10, in particular to the housing 31 of the camera head 30 of the video endoscope 10, as shown in FIG. 5, may occur by means of a vacuum, which can be generated, for example, via an additional suction opening 41 in an intermediate space 44a between the housing 31 and the proximal end of the hollow tube 71.

If an exhaust air opening 42 is provided in the video endoscope 10 and an exhaust valve 76 is provided in the envelope 76, the connecting element 43 of the exhaust air opening 42 and the connecting element 77 of the exhaust valve 76 can preferably be coupled when the hollow tube 71 is fixed to the video endoscope 10, in particular to the housing 11, so that, when the vacuum pump 40 is activated, the air suctioned by the vacuum pump 40 can be conveyed out of the video endoscope 10 and the envelope 70 through the exhaust air opening 42 and the exhaust valve.

After inserting the video endoscope 10 into the envelope 70, the inlet opening 74 can be closed by means of the closure 75. Subsequently, the vacuum pump 40 may be activated and air may be suctioned from the intermediate space between the video endoscope 10 and the envelope 70 to suction the envelope 70 against the surface of the video endoscope 10. In particular, a negative pressure is created in the envelope 70. The pressure prevailing in the envelope 70 can be detected by means of the pressure sensor 50 and, in particular, continuously monitored, for example, by comparing the prevailing pressure with a predetermined threshold value or by comparing the prevailing pressure with the pressure outside the envelope 70, which can be detected, for example, by means of a further pressure sensor, which is not shown, in the exhaust air opening 42. If the prevailing pressure exceeds the threshold value or if the difference between the prevailing pressure and the pressure outside the envelope falls below a threshold value, this may indicate leakage of the envelope 70, possibly caused by a defect of the sterile barrier. Therefore, in this case, an alarm signal may be issued, for example by a display on the display and control unit 36 and/or by means of an audible warning signal.

After an operation, the video endoscope 10, in particular the camera head 30, can be placed on a charging station, which is not shown, for charging of the accumulator 61. The charging station can, in particular, be located in the operating room.

FIG. 6 shows a video endoscope 10', which in substance differs from the video endoscopes 10 described above in the shape of the housing 31 of the camera head 30. In the present embodiment example, the adjustable foot or feet 32 are enclosed by the housing 31, in which the display and control unit 36 is arranged. The housing 31 may, in particular, include only a single adjustable foot 32. The video endoscope 10' may be positioned directly on the body of a patient 100, as shown in FIG. 6. A particularly safe positioning is possible if the suction cup 33 of the adjustable foot 32 or the suction cups 33 of the adjustable feet 32 are suctioned onto the body of the patient 100, in particular by means of the vacuum pump 40. The pressure at the suction cups 33 can be monitored and an alarm can be issued if a suction cup 33 is released. An operator 110 can view the video image by means of a conventional monitor (which is not shown) or preferably, as shown, by means of a head-mounted display 111 and can control the camera, for example, by means of voice commands. The voice commands may relate, for example, to brightness, focus and/or image detail by means of zoom-in or zoom-out.

FIGS. 7a and 7b illustrate a flushing device 80 that can be used with the video endoscopes 10, 10' described above. The flushing device 80 has a flushing fluid bag 85 in which a flushing fluid 83, for example a saline solution, is arranged. The flushing fluid bag 85 is made of a flexible material. When pressure is applied to the flushing fluid bag 85, the flushing fluid 83 is expelled from the flushing fluid bag 85.

The flushing fluid bag 85 is arranged in a vacuum bag 84, which can be connected to the vacuum pump 40 via a vacuum connection 81. A negative pressure can be generated in the vacuum bag 84 by means of the vacuum pump 40, which negative pressure thereby causes the vacuum bag 84 to contract and thereby exert a pressure on the flushing fluid bag 85, whereby the flushing fluid is expelled from the flushing fluid bag 85. The flushing fluid bag 85 is connected via a flushing connection 82 to a flushing channel 82a, which is attached, for example, to the outside of the shaft 23 of the endoscope 20. Inasmuch as the endoscope 20 is arranged in the envelope 70, the flushing channel 82a is accordingly arranged on the outside of the envelope 70. For easy arrangement of the flushing channel 82a on the shaft 23, the flushing channel 82a can, for example, be inserted into a longitudinal groove arranged on the outer side of the shaft 23. A flushing device 80 of this type can readily enable flushing and, in particular, cleaning of the endoscope optics 22. A suction channel 81a can also be provided, which can also be arranged, for example, on the outside of the shaft 23, in particular in a longitudinal groove, and which is connected, for example, to the vacuum pump 40 in such a way that the flushing fluid 83 can once again be suctioned back into it.

REFERENCE LIST

10 Video endoscope
10' Video endoscope
11 Housing
20 Endoscope
21 Housing
22 Endoscope optics
23 Shaft
24 Endoscope light source
30 Camera head
31 Housing
32 Adjustable foot
32a Articulation
32b Sub-segment
32c Sub-segment 33 Suction cup
34 Suction opening
35 Camera electronics
36 Display and control unit
36a Command button
36b Display element
36c Display element
36d Display element
37 Edge
40 Vacuum pump
41 Suction opening
42 Exhaust air opening
43 Connecting element
44a Intermediate space
44b Intermediate space
45 Compressed air container
50 Pressure sensor
60 Power supply
61 Accumulator
62 Radio interface
70 Envelope
71 Hollow tube
71a Distal end
71b Proximal end
71c Channel
72 Window
72a Spacer
72b Free space
73 Pouch
74 Inlet opening
75 Closure
76 Exhaust valve
77 Connecting element
78 Collar
79 Bayonet lock
80 Flushing device
81a Suction channel
82 Flushing connection
82a Flushing channel
83 Flushing fluid
84 Vacuum bag
85 Flushing fluid bag
100 Patient
110 Operator
111 Head-mounted display

The invention claimed is:

1. A video endoscope (10) with an endoscope (20) comprising endoscope optics (22) and a camera head (30) comprising camera electronics (35) and a display and control unit (36),
wherein a vacuum pump (40) is arranged in the video endoscope (10) for aspiration of air from the environment of the video endoscope (10),
wherein the video endoscope (10) comprises a housing (11) in which the vacuum pump (40) is arranged, wherein a suction opening (41) for the vacuum pump (40) is arranged in the wall of the housing (11), and
wherein an exhaust air opening (42) is arranged in the wall of the housing (11), wherein the exhaust air opening is connected to an exhaust valve (76) of an envelope (70) for the video endoscope (10).

2. The video endoscope according to claim 1, characterized in that a compressed air container (45) is provided for receiving the suctioned air.

3. The video endoscope according to claim 1, characterized in that the video endoscope (10) comprises at least one pressure sensor (50), for example for determining the ambient pressure.

4. The video endoscope according to claim 1, characterized in that the video endoscope (10) comprises a wireless power supply (60).

5. The video endoscope according to claim 1, characterized in that the video endoscope (10) comprises a radio interface (62).

6. The video endoscope according to claim 1, characterized in that the housing (11) comprises at least one adjustable foot (32), preferably three adjustable feet (32), which comprises at least one suction cup (33), which is preferably connected to the vacuum pump (40).

7. The video endoscope according to claim 1, characterized in that the display and control unit (36) comprises a touch display (36).

8. The video endoscope according to claim 1, characterized in that the display and control unit (36) is surrounded by a circumferential edge, wherein at least one suction opening (41) of the vacuum pump (40) is arranged in the circumferential edge (37).

9. The video endoscope according to claim 1, characterized in that a vacuum bag (84) is provided which is connectable to the vacuum pump (40) and in which a flushing fluid bag (85) is arranged.

10. The video endoscope according to claim 1, characterized in that the endoscope (20) is detachably connected to the camera head (30) and can preferably be locked in place by negative pressure generated by the vacuum pump (40).

11. The video endoscope (10) of claim 1, comprising an envelope (70) suitable to receive a video endoscope (10) comprising a hollow tube (71) having a distal end (71a) and a proximal end (71b), wherein the distal end (71a) is closed by means of an optically transparent window (72), wherein a flexible pouch (73) having an inlet opening (74) is arranged at the proximal end (71b), characterized in that the envelope (70) comprises an exhaust valve (76).

12. The video endoscope according to claim 11, characterized in that the exhaust valve (76) is connected to an exhaust air opening (42) of the vacuum pump (40) of the video endoscope (10) disposable in the envelope (70).

13. The video endoscope according to claim 11, characterized in that the exhaust valve (76) is implemented as a one-way check valve.

14. The video endoscope according to claim 11, characterized in that the inlet opening (74) of the pouch (73) is implemented to be closable by means of a closure (75).

15. The video endoscope according to claim 11, characterized in that the hollow tube (71) has at its proximal end (71b) a circumferential collar (78) in which the exhaust valve (76) is arranged.

16. The video endoscope according to claim 11, characterized in that the hollow tube (71) is made of metal or a similarly sturdy material that is resistant to tension and pressure.

17. The video endoscope according to claim 11, characterized in that the pouch (73) is made of a transparent plastics material.

18. The video endoscope according to claim 11, characterized in that a channel (71c) is arranged in the hollow tube (71) running between the distal end (71a) and the proximal end (71b).

19. The video endoscope according to claim 11, characterized in that the hollow tube (71) is detachably fixable to the video endoscope (10).

20. The video endoscope according to claim 19, characterized in that an exhaust air opening (42) is arranged in the wall of the housing (11) of the video endoscope (10), the exhaust air opening (42) being connected to an exhaust valve (76) of the envelope (70) for the video endoscope (10), that an exhaust valve (76) is arranged in the envelope (70) for the video endoscope (10), the exhaust valve (76) being connected to the exhaust air opening (42) of the housing (11) of the video endoscope (10).

21. A video endoscope (10) with an endoscope (20) comprising endoscope optics (22) and a camera head (30) comprising camera electronics (35) and a display and control unit (36), wherein a vacuum pump (40) is arranged in the video endoscope (10) for aspiration of air from the environment of the video endoscope (10), and wherein the endoscope (20) is detachably connected to the camera head (30) and can be locked in place by negative pressure generated by the vacuum pump (40).

* * * * *